United States Patent
Kannengiesser et al.

(10) Patent No.: US 10,613,177 B2
(45) Date of Patent: Apr. 7, 2020

(54) METHOD AND MAGNETIC RESONANCE APPARATUS FOR DETERMINING A SCANNING REGION RELEVANT TO A MAGNETIC RESONANCE EXAMINATION

(71) Applicant: Siemens Healthcare GmbH, Erlangen (DE)

(72) Inventors: Stephan Kannengiesser, Wuppertal (DE); Michael Wullenweber, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 477 days.

(21) Appl. No.: 15/248,083

(22) Filed: Aug. 26, 2016

(65) Prior Publication Data

US 2017/0059678 A1   Mar. 2, 2017

(30) Foreign Application Priority Data

Aug. 27, 2015   (DE) .................. 10 2015 216 405

(51) Int. Cl.
| | | |
|---|---|---|
| *G01R 33/54* | (2006.01) | |
| *A61B 5/055* | (2006.01) | |
| *A61B 5/00* | (2006.01) | |
| *G16H 40/63* | (2018.01) | |

(52) U.S. Cl.
CPC ............ *G01R 33/54* (2013.01); *A61B 5/0037* (2013.01); *A61B 5/055* (2013.01); *G01R 33/543* (2013.01); *G16H 40/63* (2018.01)

(58) Field of Classification Search
CPC ............ G01R 33/3854; G01R 33/4822; G01R 33/4833; G01R 33/5617; G01R 33/4826; G01R 33/54; G01R 33/543; A61B 5/0037; A61B 5/055
See application file for complete search history.

(56) References Cited

U.S. PATENT DOCUMENTS

| | | | |
|---|---|---|---|
| 2003/0094947 A1* | 5/2003 | Akgun ................... | A61B 5/055 324/309 |
| 2005/0119565 A1* | 6/2005 | Pescatore ................ | A61B 6/08 600/429 |
| 2007/0038070 A1 | 2/2007 | Tank | |
| 2007/0232895 A1 | 10/2007 | Wohlfarth | |
| 2011/0044524 A1* | 2/2011 | Wang ..................... | G01R 33/54 382/131 |
| 2013/0123608 A1* | 5/2013 | Consiglio ............ | A61B 5/0002 600/410 |
| 2013/0129174 A1* | 5/2013 | Grbic .................... | G06T 7/0012 382/131 |

(Continued)

*Primary Examiner* — Christopher P McAndrew
*Assistant Examiner* — Zannatul Ferdous
(74) *Attorney, Agent, or Firm* — Schiff Hardin LLP

(57) ABSTRACT

In a method and magnetic resonance apparatus for determining a scanning region that is relevant to a magnetic resonance examination, overview data are acquired from an object positioned on a patient accommodation device during total imaging, the overview data are evaluated so as to generate position information therefrom relating to the object positioned on the patient accommodation device on the basis of the overview data, and the scanning region that is relevant to the magnetic resonance examination is determined on the basis of the position information.

11 Claims, 2 Drawing Sheets

(56) References Cited

U.S. PATENT DOCUMENTS

| | | | |
|---|---|---|---|
| 2013/0154641 A1* | 6/2013 | Grodzki | G01R 33/56572 |
| | | | 324/309 |
| 2013/0279779 A1* | 10/2013 | Darrow | G01R 33/543 |
| | | | 382/131 |
| 2018/0116621 A1* | 5/2018 | Berker | A61B 5/0035 |
| 2018/0210052 A1* | 7/2018 | Ham | A61B 5/0555 |

* cited by examiner

METHOD AND MAGNETIC RESONANCE APPARATUS FOR DETERMINING A SCANNING REGION RELEVANT TO A MAGNETIC RESONANCE EXAMINATION

BACKGROUND OF THE INVENTION

Field of the Invention

The present invention concerns a method for determining a scanning region relevant to a magnetic resonance examination. The present invention further relates to a magnetic resonance device that is designed to implement such a method.

Description of the Prior Art

In magnetic resonance examinations that make use of whole body images of a patient, the scanning region has to be selected so as to be very large in order to ensure that the entire patient is scanned. This often results in too large a scanning region being specified, such that even regions in which no part of the patient is situated are scanned or affected by the scanning. This leads to very long scan times for the magnetic resonance examination.

The scanning region is generally set or entered as an input manually by medical personnel responsible for operating the magnetic resonance apparatus, such as a physician and/or a medical technician. In addition, the fact that patients of various body sizes are to be examined makes the designation of the scanning region more difficult, because there are different sizes involved for the relevant scanning region.

SUMMARY OF THE INVENTION

An object of the present invention is to provide a simple and dynamic adjustment of the scanning region for a magnetic resonance examination with respect to the size of the patient.

The method according to the invention for determining a scanning region relevant to a magnetic resonance examination has the following steps. Overview data are obtained for an object positioned on a patient accommodation device during total imaging of the object. The overview data are evaluated in a processor in order to generate position information relating to the object positioned on the patient accommodation device on the basis of the overview data. The scanning region relevant to a magnetic resonance examination is determined in the processor on the basis of the position information.

In this context, a scanning region means a set region for which the magnetic resonance examination is intended to be carried out. The scanning region and/or the set region can be determined with respect to the patient accommodation device. Furthermore, a relevant scanning region means a scanning region that includes, for example, the body region of a patient that is to be investigated or an extent of an examination phantom. For a magnetic resonance examination, the relevant scanning region is moved into an isocenter region of a patient accommodating region of the magnetic resonance scanner, in which isocenter region the total imaging and/or the magnetic resonance measurements ensue. The isocenter region includes the isocenter of the magnetic resonance scanner.

The object positioned on the patient accommodation device can be a patient positioned or a measurement phantom, as is used for calibration measurements and/or test measurements.

The total imaging preferably is implemented with a rapid data acquisition sequence, wherein an overview of the examination region and/or planning of the magnetic resonance examination can be achieved on the basis of the overview data. The total imaging typically is implemented with a lower local resolution than a diagnostic measurement, with the total imaging being able to include the whole body of a patient who is to be examined. In addition, movement of the patient table on which the patient is positioned for the magnetic resonance examination can take place during the total imaging, in particular continuous movement. The total imaging is preferably automatically controlled by a system control computer of the magnetic resonance device. For example, the total imaging can be a TimCT-measurement (Total Imaging Matrix Continuous Table movement measurement). The overview data include the data acquired during the total imaging.

Furthermore, position information means information indicating whether at least one partial region of the object that is positioned on the patient accommodation device, such as whether the patient on the patient accommodation device is positioned at a specific location, and/or a specific position of the patient accommodation device.

The invention allows a simple and dynamic adjustment of the scanning region to a patient size for a magnetic resonance examination. The relevant scanning region can be restricted to a region of the patient accommodation device that is occupied by the patient. In addition, this allows a time-saving measurement, since it is possible to dispense with the acquisition of measurement data in a region in which the patient is not situated.

This dynamic adjustment of the relevant scanning region can be used particularly advantageously in the case of whole body scans, since the relevant scanning region here is dependent on the patient size and/or coincides therewith, and consequently the relevant scanning region can be adjusted to the patient size in a simple manner using the position information that has been acquired. In a whole body scan, the patient accommodation device on which the object is situated can be continuously moved and/or transported into the patient accommodation region.

The magnetic resonance examination is carried out by a magnetic resonance apparatus. For this purpose, the magnetic resonance apparatus has a data acquisition scanner and an evaluation computer, with the overview data from the total imaging being acquired by the data acquisition scanner. The evaluation of the overview data, in particular the determination and/or generation of the patient information, is achieved automatically and/or independently by the evaluation computer, and the determination of the scanning region relevant to the magnetic resonance examination is achieved automatically and/or independently.

Furthermore, at least one end position for the scanning region relevant to the magnetic resonance examination can be determined on the basis of the position information. As a result, the relevant scanning region can be adjusted automatically and/or independently to the end position of the subject positioned on the patient accommodation device, in particular of a patient and/or of an examination phantom. The end position of the object positioned on the patient accommodation device is preferably dependent on the size of the object and occur at various positions for different objects. A further advantage is that a manual entry of the end position of the scanning region, for which a medical technician must conventionally make a rough estimate of the size of the object, can be dispensed with. Moreover, unwanted errors in the determination of the end position can be avoided.

The end position defines a position, up to which an extent of the object positioned on the patient accommodation device extends. The end position is situated on the object in the direction of movement of the patient accommodation device. In particular, the end position is that region of the object situated on the patient accommodation device that the object reaches when the object is moved into the patient accommodation region, and hence an isocenter of the magnetic resonance device. Consequently, the end position is that region in which the total imaging is carried out last.

In a further embodiment of the invention, for the scanning region relevant to the magnetic resonance examination, a starting position is determined on the basis of the position information. As a result, the relevant scanning region can be adjusted automatically and/or independently to a patient size of the object positioned on the patient accommodation device, in particular a patient and/or an examination phantom. The starting position of the object situated on the patient accommodation device can be a function of a size of the object or of the type of examination, such as when a specific magnetic resonance examination requires a very precisely defined position of the patient. A further advantage is that a manual entry of the starting position of the scanning region, for which a medical technician must conventionally make a rough estimate of the size of the object, can be avoided. Unwanted errors in the determination of the starting position thus can be prevented.

The starting position defines a position in which a positioning region of the object positioned on the patient accommodation device begins, the starting position being situated anteriorly on the object in the direction of movement of the patient accommodation device. In particular, the starting position is that region of the object positioned on the patient accommodation device that, when the object moves into the patient accommodation region, is first to reach the patient accommodation region and hence an isocenter of the magnetic resonance device. Consequently, the starting position is that region in which the total imaging is carried out first.

In a further embodiment of the invention, the acquisition of the overview data, the evaluation of the overview data, and the determination of the scanning region relevant to the magnetic resonance examination, ensue continuously during the total imaging. It is preferable for a patient table, on which the object to be examined and/or the patient is located, to be moved and/or transported continuously through the isocenter of the magnetic resonance scanner. As a result, an evaluation of the overview data and the determination of the relevant scanning region can be achieved during the measurement that is in progress. This makes it possible to firmly set a starting point and/or a finishing point of the relevant scanning region, even when the measurement is in progress. The total imaging can be terminated once the end position has been attained, such that a particularly time-saving total imaging can be achieved.

Furthermore, the evaluation of the overview data can include a sub-division of the overview data into two or more transverse slices and at least one item of position information is determined for each of the two or more transverse slices. In this case, at least one item of position information can be generated for each slice that is essentially perpendicular to the movement direction of the patient accommodation device. This allows a precise determination of the scanning region relevant to the ongoing magnetic resonance examination.

In a further embodiment of the invention, for the evaluation of the overview data, at least one item of pixel information relating to at least one of the two or more transverse slices is compared with a threshold value, the position information being determined dependent on the comparison of the at least one item of pixel information with the threshold value. This allows a simple and rapid determination of the position information such that the relevant scanning region can be available for a magnetic resonance examination immediately, or soon after the total imaging.

Furthermore, values from at least two or more pixels from the transverse slice are entered into the processor as an input for the determination of the at least one item of pixel information. As a result, a mean value can be determined over a number of pixels from at least one of the two or more transverse slices, and consequently measurement inaccuracies in individual pixels from the transverse slice can be minimized. As a result, a particularly precise determination of position information can be provided.

In another embodiment of the invention, the magnetic resonance examination is carried out on an object positioned on the patient accommodation device as a function of the relevant scanning region. As a result, a particularly time-saving magnetic resonance examination can be carried out since the magnetic resonance examination can be restricted to regions in which, for example, a patient or an examination phantom is situated. Regions in which there is no examination object are not taken into account in the magnetic resonance examination and/or are excluded.

In another embodiment of the invention, the speed of the patient accommodation device during the magnetic resonance examination is set as a function of the relevant scanning region. In this way, regions that include, for example, end regions of the patient accommodation device and in which no patient is situated, are transported through the isocenter of the magnetic resonance device at a faster speed than regions of the patient accommodation device in which the patient is situated. This allows the scan time for the magnetic resonance examination to be shortened, since the magnetic resonance examination can be restricted exclusively to those regions that are included in the relevant scanning region.

Furthermore, the invention encompasses a magnetic resonance apparatus that is designed to implement a method for determining a scanning region relevant to a magnetic resonance examination. The apparatus has a data acquisition scanner that is operated to acquire overview data relating to an object positioned on a patient accommodation device of the scanner during a total imaging of the object. The apparatus also has an evaluation computer that evaluates the overview data as to generate patient information relating to the object positioned on the patient accommodation device on the basis of the overview data. The evaluation computer determines the scanning region relevant to the magnetic resonance examination on the basis of the position information.

The inventive apparatus allows a simple and dynamic adjustment of the scanning region to a patient size for a magnetic resonance examination. The relevant scanning region can be restricted to a region of the patient accommodation device that is actually occupied by the patient. This allows a time-saving measurement, since it is possible to dispense with the acquisition of measurement data in a region in which the patient is not situated.

This dynamic adjustment of the relevant scanning region can be used particularly advantageously in the case of whole body scans on the patient since the relevant scanning region here is dependent on the patient size and/or coincides therewith, and consequently the relevant scanning region can be adjusted to the patient size in a simple manner using the position information that has been acquired. In a whole body scan, the patient accommodation device on which the object is situated is preferably moved and/or transported continuously into the patient accommodation region.

The advantages of the magnetic resonance device according to the invention essentially correspond to the advantages of the method according to the invention for determining a scanning region relevant to a magnetic resonance examination, as described above. Features, advantages, and alternative embodiments mentioned above are applicable to the apparatus as well.

The invention further encompasses a non-transitory, computer-readable data storage medium encoded with program code, which is directly loadable into a computer program product, which includes a program and which is directly loadable into a memory of a programmable evaluation computer of a magnetic resonance apparatus. The program code causes the inventive method for determining a scanning region relevant to a magnetic resonance examination to be executed when the program code is executed in the evaluation computer. The program code may require peripherals, such as libraries and auxiliary functions, in order to implement the corresponding embodiments of the method.

DESCRIPTION OF THE PREFERRED EMBODIMENTS

Figure 1:
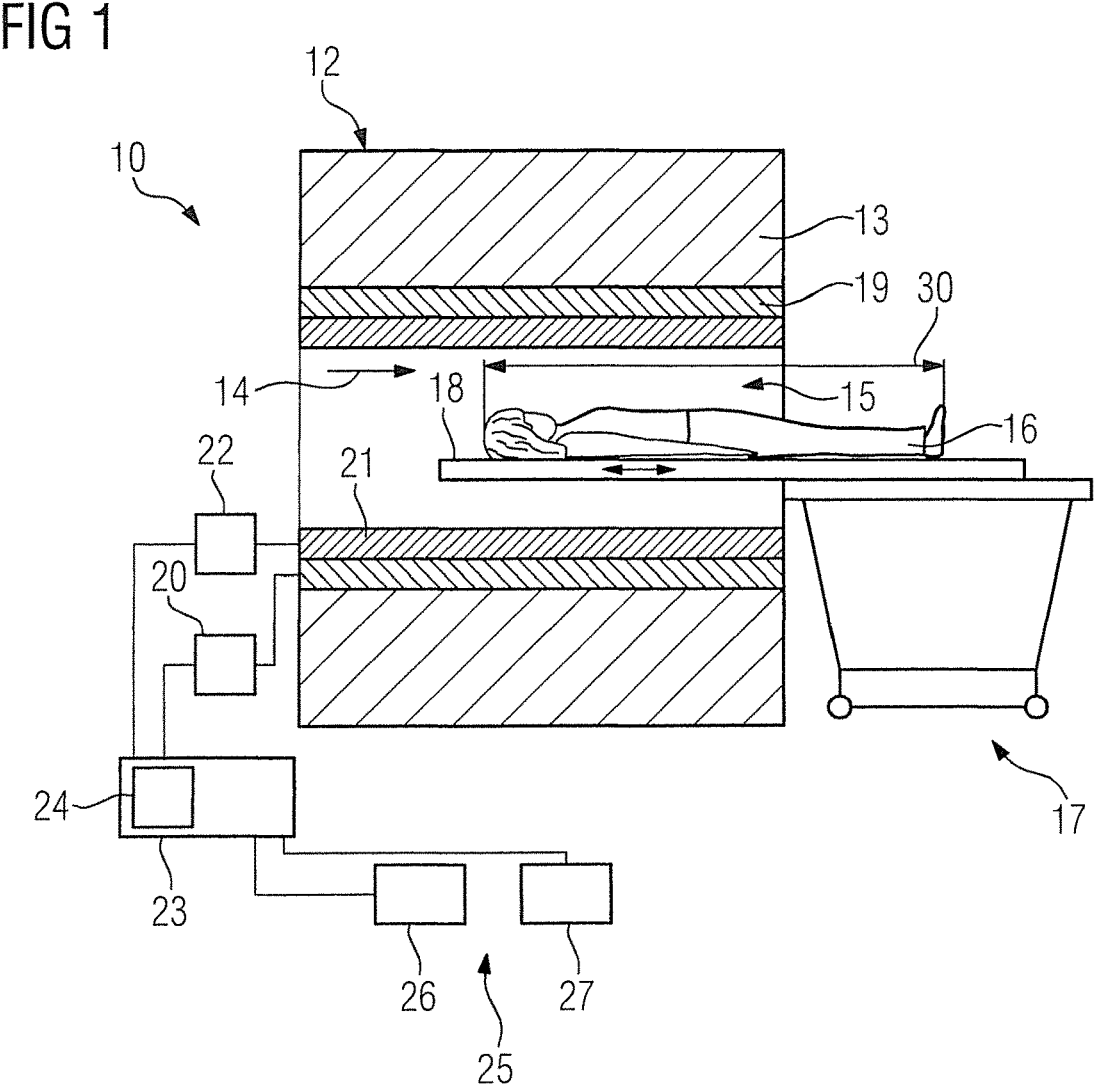
FIG. 1 schematically illustrates a magnetic resonance apparatus according to the invention.

FIG. 1 schematically illustrates a magnetic resonance apparatus 10. The magnetic resonance apparatus 10 includes a data acquisition scanner 12. The data acquisition scanner 12 includes a superconducting basic field magnet 13 that generates a strong and constant basic magnetic field 14. The scanner 12 has a cylindrical patient accommodation region 15 to reserve an examination object, such as a patient 16. The examination object can also be an examination phantom.

In the present embodiment, the patient accommodation region 15 is cylindrical in design and is cylindrically surrounded in a circumferential direction by the data acquisition scanner 12. A design of the patient accommodation region 15 that deviates therefrom is also conceivable. The patient 16 can be moved by a patient accommodation device 17 of the magnetic resonance apparatus 10 into the patient accommodation region 15. The patient accommodation device 17 has for this purpose a patient bed 18 that is moveable inside the patient accommodation region 15.

The data acquisition scanner 12 further has a gradient coil unit 19 that generates magnetic field gradients that are used for spatial encoding during an imaging procedure. The gradient coil unit 19 is controlled by a gradient control processor 20 of the magnetic resonance apparatus 10. The data acquisition scanner 12 further has a radio frequency antenna 21 that is controlled by a radio frequency antenna control processor 22 so as to emit radio-frequency magnetic resonance sequences into an examination space that is essentially formed by the patient accommodation region 15 of the magnetic resonance apparatus 10. The radio-frequency sequences give certain nuclear spins in the patient 16 a magnetization that causes those nuclear spins to deviate from the polarization (alignment) produced by the basic magnetic field 14. As those nuclear spins relax after this excitation thereof, they emit magnetic resonance signals, which are also radio-frequency signals.

To control the basic field magnet 13, the gradient control processor 20, and to control the radio frequency antenna control processor 22, the magnetic resonance apparatus 10 has a system control computer 23. The system control computer 23 centrally controls the magnetic resonance apparatus 10, such as for example, to execute a predetermined gradient echo imaging sequence. The system control computer 23 includes an evaluation processor 24 to evaluate medical image data that are acquired during the magnetic resonance examination. Here, the evaluation processor 24 is incorporated within the system control computer 23.

The magnetic resonance apparatus 10 further has a user interface 25, which is connected to the system control computer 23. Control information, such as imaging parameters, as well as reconstructed magnetic resonance images, can be displayed to a medical technician on a display unit 26, such as at least one monitor of the user interface 25. The user interface 25 further has an input unit 27, via which the information and/or parameters can be entered by the medical technician during a measurement procedure.

The system control computer 23, in particular the evaluation processor 24 of the system control computer 23, is designed along with the data acquisition scanner 12 to carry out a method according to the invention for determining a scanning region 30 relevant to a magnetic resonance examination. For this purpose, the system control computer 23, in particular the evaluation processor 24 thereof, has appropriate software and/or computer programs that cause the method for determining a scanning region 30 that is relevant to a magnetic resonance examination to be executed. The computer programs and/or software are stored in a memory, which is not shown in further detail and which is preferably encompassed by the system control computer 23. The program code also can be stored in a computer-readable data carrier.

At the start of the method according to the invention, an object 28 that is to be examined is already positioned in an examination position on the patient accommodation device 17, in particular on the patient table 18 of the patient accommodation device 17. In the present embodiment, the object 28 that is to be examined takes the form of a patient 16. Basically, the object 28 that is to be examined could also be an examination phantom, as is advantageous for calibration measurements, or further objects that are reasonable to those skilled in the art.

In a first process step 100, overview data are acquired from the object 28 that is positioned on the patient accommodation device 17, namely the patient 16, during total imaging. The acquisition of the overview data during total imaging ensues by operation of the data acquisition scanner 12 of the magnetic resonance apparatus 10. In the present embodiment, the total imaging is a whole-body measurement in which the patient 16 is transported continuously into the patient accommodation region 15, such as a TIMCT (Total Imaging Matrix Continuous Table Move) measurement. The patient table 18 on which the patient 16 is positioned is moved and/or transported at a continuous speed into the patient accommodation region 15. While the patient 16 is being transported continuously into the patient accommodation region 15, at the same time the overview data are acquired by the data acquisition scanner 12. For this purpose, local radio frequency antenna units are preferably placed on the patient 16, with the field of these local radio frequency antenna units collectively covering the whole body of the patient 16.

In a subsequent process step 101, the overview data that have been acquired are transmitted to the evaluation processor 24, in which they are evaluated. To transmit the overview data, the magnetic resonance apparatus 10 has a data transfer unit that transfers the data in a cable-free (wireless) manner such as by WLAN, WIFI, etc.

In process step 101, one or more items of position information relating to the object 28 that is positioned on the accommodation device 17, in particular the patient 16 positioned on the patient table 18, is/are generated on the basis of the overview data that have been acquired. For this purpose, the evaluation of the overview data includes a subdivision of the overview data into two or more transverse slices, wherein at least one item of position information is determined by the evaluation processor 24 for each of the two or more transverse slices.

Figure 3:
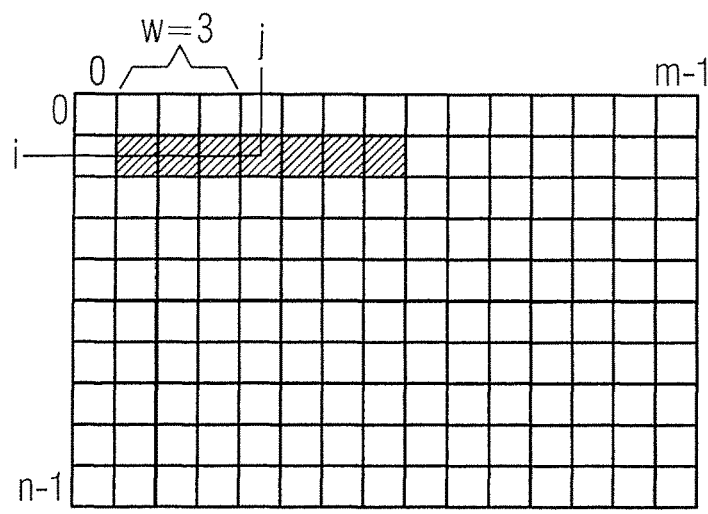
FIG. 3 schematically illustrates the determination of position information for a slice.

An example of a determination of the position information made by the evaluation processor 24 is a comparison, and is shown schematically in FIG. 3. Here, at least one item of pixel information relating to at least one of the two or more transverse slices is compared by the evaluation unit 24 with a threshold value $msl_{threshold}$. The pixel information includes a maximum moving-average value $msl_{max}$ and is preferably determined as a mean value msl, in particular a running average value msl, from at least two or more pixels from the transverse slice (FIG. 3).

The running average value msl over a window with the size 2*w+1 for a pixel (i,j) from a slice with n lines and j columns is determined as:

$$msl(i, j) = \sum_{n=-w}^{w} \text{image}(i, j+n)$$

The size of the window is preferably determined at w=5. Alternatively, w can have for this purpose further values that appear reasonable to those skilled in the art, such as w=4 or w=3 or w=6, etc.

A maximum moving average value $msl_{max}$ for a slice is determined as:

$$msl_{max} = \max_{0<i<n-1; w<j<m-w-1} msl(i, j)$$

If the pixel information, namely the maximum running average value $msl_{max}$, is above the threshold value, then the slice is seen and/or interpreted as being within the object 28, in particular as within the patient 16. Conversely, if the maximum moving average value $msl_{max}$ is below the threshold value, then the slice is seen as being outside the object 28, in particular as outside the patient 16. In practice, a threshold value of 50, at which a clear distinction can be made between regions 31 in which the object 28, in particular the patient 16, is situated, and regions 32 in which no object 28, in particular no patient 16, is situated, and that consequently are object-free or patient-free regions 32, has proved to be advantageous. The regions 31 in which an object 28 is situated and the object-free regions 32 occur consecutively in the direction of the longitudinal extent 33 of the patient table 18.

Other threshold values that appear reasonable to those skilled in the art may also be used. In an alternative embodiment of the invention, the determination of the position information can also include further methods of calculation that appear reasonable to those skilled in the art.

Figure 4:
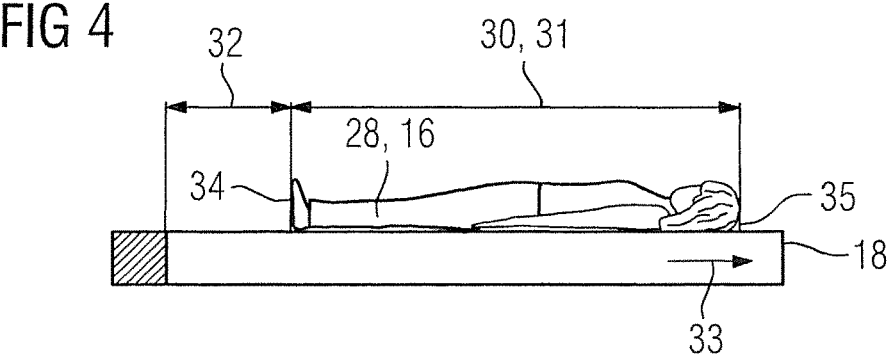
FIG. 4 shows a relevant scanning region.

In a further process step 102, the scanning region 30 relevant to the magnetic resonance examination is determined automatically and/or independently by the evaluation processor 24 on the basis of the position information. Here, an end position 34 of the scanning region 30 relevant to the magnetic resonance examination is determined by the evaluation processor 24 on the basis of the position information. In the present embodiment, the end position 34 is the posterior end of the patient 16, the end position 34 being situated at the rear in the direction of the movement direction 29 (FIG. 4).

Alternatively or additionally, a starting position 35 can be determined by the evaluation processor 24 for the scanning region 30 that is relevant to the magnetic resonance examination. In the present embodiment, the starting position 35 is the anterior end of the patient 16, the starting position 35 being situated anteriorly in the direction of the movement direction 29. With the use of the end position 34 and/or the starting position 35, the relevant scanning region 30 can be determined automatically by the evaluation processor 24 (FIG. 4).

Process steps 100, 101 and 102 are repeated continuously during the total imaging so that the acquisition of the overview data, the evaluation of the overview data, and the determination of the scanning region 30 relevant to magnetic resonance examination can be made continuously during the total imaging. It is advantageous in this context that the object 28 (patient 16) positioned on the patient table 18 is moved continuously into the patient accommodation region 15 and hence also moved into an isocenter of the data acquisition scanner 12, so that a continuous acquisition of overview data is possible. Directly and indirectly, object-free or patient-free regions 32 can be distinguished by the evaluation processor 24 from regions 31, in which an object 28 and/or the patient 16 is situated, and the relevant scanning region 30 can be determined. This also allows for the measurement to be terminated automatically and/or independently by the evaluation processor 24 when the end position 34 is reached.

Figure 2:
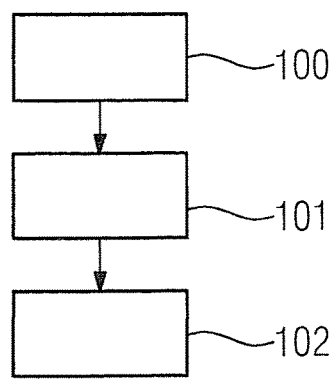
FIG. 2 is a flowchart of the method according to the invention for determining a scanning region relevant to a magnetic resonance examination.
Figure 5:
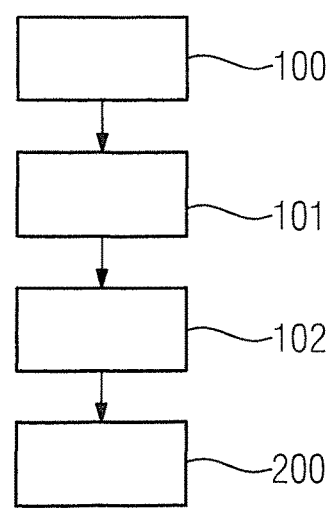
FIG. 5 is a flowchart of another embodiment of the method according to the invention.

FIG. 5 schematically shows an alternative embodiment to FIG. 2 of the method for determining a scanning region 30 relevant to a magnetic resonance examination. Process steps 100 to 102 are designed by analogy with process steps 100 to 102 in FIG. 2, such that reference is made in this respect to the description of FIG. 2.

The method according to FIG. 5 has a further process step 200, in which a magnetic resonance examination is carried out on the object 28 that is positioned on the patient accommodation device 17, in particular on the patient positioned on the patient table 18, dependent on the relevant scanning region 30 that has been determined. In this process step 200, the magnetic resonance examination is restricted only to the relevant scanning region 30.

Furthermore, in this further process step 200, the speed of movement of the patient table 18 can be set automatically and/or independently during the magnetic resonance examination as dependent on the relevant scanning region 30 by the system control computer 23, in particular by the evaluation processor 24. Regions 32 of the moveable patient table 18, on which no part of the patient 16 is situated, and hence for which no magnetic resonance data need to be acquired, can be transported through the isocenter of the magnetic resonance device 10 at a higher speed.

Conversely, regions 31 of the moveable patient table 18 that are occupied by the object to be examined 28, in particular the patient 16, are transported at a slower speed into the patient accommodation region 16, in particular through the isocenter.

In an alternative embodiment of the invention, the total imaging and also the subsequent magnetic resonance examination can be restricted to only a partial region of the patient 16, with marker elements being used to determine the starting position 35 and end position 34. These elements are positioned on the object 28 to be examined and/or on a local radio frequency antenna unit.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for conducting a magnetic resonance (MR) examination using an MR data acquisition scanner that has an isocenter, said method comprising:
   operating said MR data acquisition scanner to execute a total MR overview imaging sequence of a patient on a patient table of the MR data acquisition scanner so as to acquire MR overview data that represent an entirety of the body of the patient and at least a portion of a surface of the patient table next to the body of the patient, by continuously moving the patient on the patient table through the MR data acquisition scanner;
   providing the MR overview data to a processor and, in said processor, automatically evaluating the MR overview data to produce position information therefrom that identify a region of said patient table occupied by said patient and a region of said patient table that is not occupied by said patient;
   in said processor, using said position information to determine, while the MR overview data is being acquired by continuously moving the patient on the patient table through the MR data acquisition scanner, a scanning region for conducting a whole body MR diagnostic examination of the patient, in which the patient also will be moved continuously through the isocenter of the MR data acquisition scanner by continuously moving the patient table in a single direction with respect to the MR data acquisition scanner during the whole body MR diagnostic examination of the patient while the MR data acquisition scanner remains stationary, with said scanning region being limited to said region occupied by the patient and excluding said region not occupied by the patient;
   in said processor, determining an end position of said patient that is a last part of said region occupied by the patient to pass through the isocenter during the continuous movement of the patient in said whole body MR diagnostic examination, and determining a starting position of the patient that is a first part of said region occupied by the patient to pass through said isocenter during continuous movement of the patient in said whole body MR diagnostic examination;
   in said processor, generating control signals for operating said MR diagnostic scanner to conduct said whole body MR diagnostic examination, with said control signals limiting acquisition of MR data in said whole body MR diagnostic examination only to said region occupied by said patient, and said control signals also including respective electronic designations of said end position and said starting position; and
   providing said control signals from said processor to said MR data acquisition scanner and thereby operating said MR data acquisition scanner to execute said whole body MR diagnostic examination and to thereby acquire MR diagnostic data only from the region occupied by patient on the patient table, and making the acquired MR data available from the processor in electronic form, as a data file.

2. A method as claimed in claim 1 comprising acquiring said overview data, evaluating said overview data, and determining said scanning region continuously during said total imaging.

3. A method as claimed in claim 1 wherein said designation of said scanning region in said electrical signal emitted from said processor includes a control instruction to terminate said diagnostic imaging when said end of position occurs.

4. A method as claimed in claim 1 wherein said designation of said scanning region in said electrical signal emitted from said processor includes a control instruction to start said diagnostic imaging when said starting of position occurs.

5. A method as claimed in claim 1 wherein said designation of said scanning region in said electrical signal emitted from said processor includes an instruction to start said diagnostic imaging when said starting position occurs and a further instruction to terminate said diagnostic imaging when said end position occurs.

6. A method as claimed in claim 1 comprising, in the evaluation of said overview data in said processor, subdividing said overview data into at least two transverse slices of said patient, and determining at least one item of position information for each of said at least two transverse slices.

7. A method as claimed in claim 6 comprising, in the evaluation of the overview data in said processor, comparing said at least one item of pixel information from at least one of said at least two transverse slices with a threshold value, and determining said position information dependent on a relationship, as determined by said comparing, of said at least one item of pixel information relative to said threshold value.

8. A method as claimed in claim 6 comprising generating said at least one item of pixel information from at least two pixels in the respective transverse slice.

9. A method as claimed in claim 1, comprising controlling said MR data acquisition scanner during said diagnostic examination dependent on said position information by moving said patient through said MR data acquisition scanner at a faster speed when said region that is not occupied by said patient is in said isocenter compared to when said region that is occupied by said patient is in said isocenter.

10. A magnetic resonance (MR) apparatus comprising:
    an MR data acquisition scanner having an isocenter;
    a processor provided with MR overview data obtained by operating said MR data acquisition scanner to execute a total MR overview imaging sequence of a patient on a patient table of the MR data acquisition scanner so as to acquire said MR overview data, which represent an entirety of the body of the patient and at least a portion of a surface of the patient table next to the body of the patient, by continuously moving the patient on the patient table through the MR data acquisition scanner;

said processor being configured to automatically evaluate the MR overview data to produce position information therefrom that identify a region of said patient table occupied by said patient and a region of said patient table that is not occupied by said patient;

said processor being configured to use said position information to determine, while the MR overview data is being acquired by continuously moving the patient on the patient table through the MR data acquisition scanner, a scanning region for conducting a whole body MR diagnostic examination of the patient, in which the patient also will be moved continuously through the isocenter of the MR data acquisition scanner by continuously moving the patient table in a single direction with respect to the MR data acquisition scanner during the whole body MR diagnostic examination of the patient while the MR data acquisition scanner remains stationary, with said scanning region being limited to said region occupied by the patient and excluding said region not occupied by the patient;

said processor being configured to also determine an end position of said patient that is a last part of said region occupied by the patient to pass through the isocenter during continuous movement of the patient in said whole body MR diagnostic examination, and to determine a starting position of the patient that is a first part of said region occupied by the patient to pass through said isocenter during continuous movement of the patient in said whole body MR diagnostic examination;

said processor being configured to generate control signals for operating said MR diagnostic scanner to conduct said whole body MR diagnostic examination, with said control signals limiting acquisition of MR data in said whole body MR diagnostic examination only to said region occupied by said patient, and said control signals also including respective electronic designations of said end position and said starting position; and said processor being configured to provide said control signals from said processor to said MR data acquisition scanner and thereby operate said MR data acquisition scanner to execute said whole body MR diagnostic examination and to thereby acquire MR diagnostic data only from the region occupied by the patient on the patient table, and to make the acquired MR data available from the processor in electronic form, as a data file.

11. A non-transitory, computer-readable data storage medium encoded with programming instructions, said storage medium being loaded into a processor of a magnetic resonance (MR) apparatus comprising an MR data acquisition scanner having an isocenter, said programming instructions causing said processor to:

receive MR overview data acquired operating said MR data acquisition scanner to execute a total MR overview imaging sequence of a patient on a patient table of the MR data acquisition scanner so as to acquire said MR overview data, which represent an entirety of the body of the patient and at least a portion of a surface of the patient table next to the body of the patient, by continuously moving the patient on the patient table through the MR data acquisition scanner;

evaluate the MR overview data to produce position information therefrom that identify a region of said patient table occupied by said patient and a region of said patient table that is not occupied by said patient;

use said position information to determine, while the MR overview data is being acquired by continuously moving the patient on the patient table through the MR data acquisition scanner, a scanning region for conducting a whole body MR diagnostic examination of the patient, in which the patient also will be moved continuously through the isocenter of the MR data acquisition scanner by continuously moving the patient table in a single direction with respect to the MR data acquisition scanner during the whole body MR diagnostic examination of the patient while the MR data acquisition scanner remains stationary, with said scanning region being limited to said region occupied by the patient and excluding said region not occupied by the patient;

determine an end position of said patient that is a last part of said region occupied by the patient to pass through the isocenter during continuous movement of the patient in said whole body MR diagnostic examination, and determine a starting position of the patient that is a first part of said region occupied by the patient to pass through said isocenter during continuous movement of the patient in said whole body MR diagnostic examination;

generate control signals for operating said MR diagnostic scanner to conduct said whole body MR diagnostic examination, with said control signals limiting acquisition of MR data in said whole body MR diagnostic examination only to said region occupied by said patient, and said control signals also including respective electronic designations of said end position and said starting position; and provide said control signals from said processor to said MR data acquisition scanner and thereby operate said MR data acquisition scanner to execute said whole body MR diagnostic examination and to thereby acquire MR diagnostic data only from the region occupied by the patient on the patient table, and make the acquired MR data available from the processor in electronic form, as a datafile.

\* \* \* \* \*